(12) United States Patent
Lundin et al.

(10) Patent No.: US 9,089,794 B2
(45) Date of Patent: Jul. 28, 2015

(54) CHROMATOGRAPHY COLUMN

(75) Inventors: Andreas Lundin, Vänge (SE); Juha Esala, Vattholma (SE)

(73) Assignee: BIOTAGE AB, Uppsala (SE)

( * ) Notice: Subject to any disclaimer, the term of this patent is extended or adjusted under 35 U.S.C. 154(b) by 674 days.

(21) Appl. No.: 13/138,855

(22) PCT Filed: Apr. 7, 2010

(86) PCT No.: PCT/EP2010/054588
§ 371 (c)(1),
(2), (4) Date: Oct. 11, 2011

(87) PCT Pub. No.: WO2010/115923
PCT Pub. Date: Oct. 14, 2010

(65) Prior Publication Data
US 2012/0037555 A1 Feb. 16, 2012

Related U.S. Application Data

(60) Provisional application No. 61/202,811, filed on Apr. 8, 2009.

(30) Foreign Application Priority Data

Apr. 8, 2009 (EP) .................................... 09157620

(51) Int. Cl.
*B01D 15/22* (2006.01)
*G01N 30/60* (2006.01)

(52) U.S. Cl.
CPC ............ *B01D 15/22* (2013.01); *G01N 30/6091* (2013.01); *G01N 30/603* (2013.01); *G01N 30/6026* (2013.01)

(58) Field of Classification Search
CPC . B01D 15/22; G01N 30/6091; G01N 30/603; G01N 30/6026
USPC ........... 210/635, 656, 659, 198.2, 198.3, 456; 96/101, 107
See application file for complete search history.

(56) References Cited

U.S. PATENT DOCUMENTS

| 3,966,609 A | 6/1976 | Godbille et al. |
| 4,557,830 A * | 12/1985 | Onitsuka et al. ........... 210/198.2 |

(Continued)

FOREIGN PATENT DOCUMENTS

| DE | 10000601 A1 | 7/2001 |
| JP | 59176670 A | 10/1984 |
| WO | WO-2007005508 A2 | 1/2007 |

OTHER PUBLICATIONS

PTO Translation No. 12-1936 of Japan Patent No. 59-176670 dated Feb. 2012.*

(Continued)

*Primary Examiner* — Ernest G Therkorn
(74) *Attorney, Agent, or Firm* — Harness, Dickey & Pierce, P.L.C.

(57) ABSTRACT

A chromatography column comprises a tubular member (1) having an open inlet end and an outlet end and being adapted to receive a packing material, and an end piece (2) inserted through the inlet end of the tubular member (1). The end piece (2) comprises a generally planar inner end portion 4, and a rounded outer end portion (5), adapted to accommodate pressure forces acting on the inner end. The end piece (2) is fixed to the inner surface of the tubular member (1) by a weld- or bond-forming joining technique based on non-contact energy transfer, preferably laser welding. A method for manufacturing a pre-packed chromatography column is also disclosed.

10 Claims, 6 Drawing Sheets

(56) References Cited

U.S. PATENT DOCUMENTS

| | | | |
|---|---|---|---|
| 4,582,608 A | | 4/1986 | Ritacco |
| 4,806,238 A | * | 2/1989 | Sattler et al. ............... 210/198.2 |
| 5,324,426 A | * | 6/1994 | Joseph et al. ............... 210/198.2 |
| 5,423,982 A | * | 6/1995 | Jungbauer et al. ......... 210/198.2 |
| 6,117,329 A | | 9/2000 | Hargro |
| 6,171,486 B1 | * | 1/2001 | Green et al. ............... 210/198.2 |
| 6,177,328 B1 | | 1/2001 | Liu et al. |
| 6,224,760 B1 | * | 5/2001 | Davies et al. .............. 210/198.2 |
| 6,365,050 B1 | * | 4/2002 | Cauchon ....................... 210/635 |
| 6,387,256 B1 | * | 5/2002 | Tuvim ........................ 210/198.2 |
| 6,398,953 B1 | | 6/2002 | Hargro |
| 6,444,122 B1 | * | 9/2002 | Van Davelaar ............ 210/198.2 |
| 8,066,875 B2 | * | 11/2011 | Ellis et al. ................. 210/198.2 |
| 8,070,957 B2 | * | 12/2011 | Ellis et al. ..................... 210/656 |
| 2002/0125181 A1 | * | 9/2002 | Pichl et al. ................. 210/198.2 |
| 2003/0102266 A1 | | 6/2003 | Ritacco |
| 2005/0082213 A1 | | 4/2005 | DeMarco |
| 2005/0133426 A1 | | 6/2005 | DeMarco |
| 2005/0161382 A1 | * | 7/2005 | Medley ...................... 210/198.2 |
| 2005/0173324 A1 | * | 8/2005 | Salven et al. .............. 210/198.2 |
| 2005/0224414 A1 | | 10/2005 | Izzo et al. |
| 2005/0242018 A1 | * | 11/2005 | Hodgin et al. ............. 210/198.2 |
| 2006/0243650 A1 | * | 11/2006 | Gebauer .................... 210/198.2 |
| 2007/0084773 A1 | | 4/2007 | DeMarco |
| 2007/0121600 A1 | | 5/2007 | Surazski et al. |
| 2007/0163102 A1 | | 7/2007 | DeMarco |
| 2008/0110814 A1 | | 5/2008 | Izzo et al. |

OTHER PUBLICATIONS

W.C. still et al., "Rapid Chromatographic Technique for Preparative Separations with Moderate Resolution", J. Org. Chem. 1978, 43, pp. 2923-2923.

European Search Report for European Patent Application No. EP 09157620.7 dated Apr. 8, 2009.

* cited by examiner

CHROMATOGRAPHY COLUMN

CROSS-REFERENCE TO RELATED APPLICATIONS

This is a 371-National Phase Application of PCT/EP2010/054588, filed Apr. 7, 2010, and claims priority under 35 U.S.C. §119 to European Patent Application No. 09157620.7, filed Apr. 8, 2009, and U.S. Provisional Application No. 61/202,811, filed Apr. 8, 2009, the entire contents of which are hereby incorporated by reference.

FIELD OF THE INVENTION

The present invention relates to liquid chromatography, and more particularly to a pressure stable column for use in the area of chemical separation as well as a method for the production of such a column packed with a separation material.

BACKGROUND OF THE INVENTION

Chromatography is a chemical separation technique utilizing the fact that substances to be separated are distributed in different ways between a stationary phase and a mobile phase. In liquid chromatography, the mobile phase is a liquid. The stationary phase, or separation medium, which typically is an adsorption medium, an ion-exchanger material, a gel or a surface-modified solid material, is usually packed in a column. Different components in a sample applied to the top of the medium bed will migrate through the column at different rates depending, e.g., on their size and degree of attraction to the stationary phase when the liquid passes through the column. Liquid chromatography is extensively used for chemical analysis as well as for preparative separations in research and industry.

In traditional chromatography, the liquid or solvent passes through the column by gravity. The rate at which the liquid passes through the column is therefore relatively slow. To speed up the rate of the chromatography process, the liquid is forced through the column by the application of a positive pressure. This may be accomplished by pumping the liquid through the column, such as in HPLC (high performance liquid chromatography), or by the application of a positive air-pressure, such as in traditional flash chromatography.

Flash chromatography is a rapid form of preparative column chromatography which dates back to 1978 (W. C. still et al., J. Org. Chem. 1978, 43, 2923-2925) and uses pre-packed disposable columns or cartridges, typically of plastic. In modern flash chromatography variants, the liquid is pumped through the column or cartridge.

The disposable columns used for flash chromatography are usually manufactured with economy in mind, which involves manufacturing the columns of inexpensive plastics and designing the columns to be easily assembled by filling the body of the column with the desired packing, usually with frit plugs on each end of the packing to hold the packing in place, and then closing the open end or ends of the columns by end pieces or caps, e.g. by screwing or snapping them to the column ends, or, more typically, attaching them by spin welding or heat plate welding.

Various column designs have been devised to improve the pressure stability and cost-efficiency in producing the columns or cartridges.

US 2003-0102266 A1 discloses a flash chromatography column assembly comprising a single-ended cartridge containing a chromatographic sorbent, and a compression head configured to cover the upper end of the cartridge and to compress the sorbent within the interior volume of the cartridge. The compression head includes a disk-shaped cover dimensioned to fit within and seal the upper end of the cartridge and a structure for transmitting a compression force to the cover to compress the sorbent in the interior volume.

WO 2007/005508 discloses a single-use chromatography column having an end plate that is fixed to the column end by spin welding. To this end, the end plate includes radially extending ridges that permit gripping by conventional spin welding equipment to spin the end plate for the purpose of a spin weld. The spin welded seal is intended to maintain its seal under higher pressures.

U.S. Pat. Nos. 6,177,328 and 6,398,953 disclose a method of supporting a media bed in a chromatography cartridge tube wherein an end cap is cooled to thermally contract the end cap to a dimension less than the inner diameter of the tube. The contracted end cap is then placed within the tube and against the media bed, and the end cap is sealed to the tube by thermal expansion of the end cap upon warming. The expansion of the end cap causes the tube to deform locally to secure the end cap within the tube.

US 2005/0161382 A1 discloses a method of forming a column for use with an analytical chemical instrument. The method comprises placing a fit in proximity of a distal end of a tube with an internal bore adapted to receive a packing material, laser welding the fit to the tube, and inserting a packing material within the internal bore of the tube. The frit is formed from a porous material, and laser welding the frit substantially reduces the volume of the porous material to leave a porous passageway through the frit.

US 2005/022414 A1 discloses a chromatography column having an inlet filter assembly which is securely fixed to the column tube by welding, heat sealing or glueing.

The prior art flash chromatography columns or cartridges, however, still have deficiencies including, for example, problems with dead volumes, insufficient pressure stability, spin welding causing melting of plastic frits, and production effectiveness.

There is therefore a need for improvements in the design of disposable plastic columns or cartridges, and especially to provide columns or cartridges which are pressure stable and can be produced in a cost-efficient way.

SUMMARY OF THE INVENTION

The above-mentioned needs are met by the present invention which provides a high pressure-stable separation column or cartridge of disposable type for chromatographic separation of chemical species as well as a method for the manufacture thereof.

Such a separation column or cartridge comprises at least one end piece which is designed (i) to be inserted into the column tube in (direct or indirect) contact with the chromatography medium and rigidly and sealingly fixed within the tube, and (ii) to withstand high pressures by having a rounded force-accommodating outer end.

In one aspect, the present invention provides a chromatographic column.

In another aspect, the present invention provides a method of preparing a pre-packed chromatography column, which method is.

In still another aspect, the present invention provides a chromatography column set as described in independent claim 15.

In yet another aspect, the present invention provides an end piece for a chromatography column as defined in independent claim 17.

Preferred embodiments of the invention are set forth in the respective dependent claims and/or are described below.

The chromatography column, or cartridge, may be of the type having open inlet and outlet ends to be closed by respective end pieces, or, alternatively, of the type having an open inlet end to be closed by an end piece, and a closed outlet with an outlet opening. In the first-mentioned case, either both the inlet end piece and the outlet end piece are designed in accordance with the present invention, or only the inlet end piece is according to present invention, whereas the outlet end piece may be of, for example, per se conventional type.

A basic feature of the present invention is thus the capability of the end piece(s) of being inserted into the column tube to a desired height and being fixed in position by a joining method based on non-contact, or contactless, energy transfer, and more particularly by such a method capable of forming a weld or bond. This makes it possible to insert the end piece into the tube to any packed media bed height, so that the flat fluid distributing part of the end piece is brought in contact with the typically used plastic filter, or frit, on top of the media bed. Thereby problems with dead volumes, as are experienced in other column or cartridge types using, for example, conventional spin or heat plate welding to fix the end piece, are effectively eliminated.

Another advantage is that also compressible chromatographic media may be packed and compressed by an end piece before fixing the end piece in position. Since it is not necessary to pack the column to a predetermined bed height, also a more effective production process is obtained. Joining the end piece to the column tube by a non-contact energy transfer method of the above-mentioned kind also permits the end piece to be pressed against the plastic frit without causing also the frit to melt as may be obtained when using e.g. spin welding.

One type of non-contact energy transfer joining methods referred to above comprises joining the components in question by converting radiation energy into thermal energy in the material of the components giving rise to a locally limited material melt in the joining area. Exemplary such methods include radiation-assisted welding techniques, such as laser welding, infrared welding and electron beam welding. Another type of such joining methods comprise radiation-assisted bonding techniques, including e.g. radiation-induced or initiated curing or hardening of an applied adhesive, such as by, for example, UV or IR radiation.

The currently preferred joining method is laser welding. In comparison with spin welding, for example, laser welding gives a relatively large weld area and thereby a stronger weld seam, thus eliminating possible weak spots in the column with regard to pressure. Optionally, a broader weld seam, or alternatively one or more additional weld seams in the joint area may be obtained by performing at least one more laser welding operation with the laser beam displaced accordingly.

To permit laser welding of two parts to each other, one of the parts need to be transparent to laser light and the other absorbing. The chromatography tube is typically at least near transparent, and the end piece, or part thereof, should therefore be laser light absorbing.

Another basic feature of the present invention is the design of the end piece with a flat inner part for contact with the frit and a rounded, typically dome-shaped outer part in force-transmitting contact with the flat inner part. This permits the use of high pressures, the forces acting upon the flat part being transferred to the dome part where they result in only pull stresses in the rounded dome (in contrast to considerable bending forces on the flat part which would result in the absence of the dome).

The terms "dome" and "dome-shaped" are to be interpreted in a broad sense herein, generally referring to the geometric configuration of a body generated by rotation of a curved line. A dome of rotary elliptical shape may be characterized by the ratio of dome height to dome bottom diameter (=the tube diameter). For the purposes of the present invention, this ratio should preferably not be less than 20%, the theoretical optimum value being 50% which corresponds to a dome having a hemispherical shape, i.e. the dome height equalling the tube radius. To make better use of the dome surface area, a practical range would be from about 20% to about 40%.

Preferably, the end piece or end pieces are assembled from two separate parts, a bottom (inner) part with a flat surface for efficient distribution of a fluid flow over the media bed cross section, and a rounded top (outer) part in pressure transmitting contact with the flat part through force transferring means extending between the top and bottom parts, such as a number of radial and/or circular supporting or stiffening flanges, ribs or the like provided on (e.g. integral with) the top (i.e. outer) face of the flat part, or, alternatively, provided on (e.g. integral with) the bottom (i.e. inner) face of the rounded top part, or optionally both in combination. The force transferring or transmitting means or structure(s) may also be or comprise a separate part or parts to be inserted between the flat bottom part and the rounded top part and assembled thereto. As still another alternative, a hydraulic liquid medium, e.g. silicone, a gel or a solidifying foam material might be contemplated as pressure transmitting medium between the flat bottom part and the pressure-optimized rounded top part.

With the above described two-part (or three-part) construction of the end piece, the top part and the bottom part may each individually be fixed to the inside of the chromatography column tube. Alternatively, only the rounded top part of the end-piece is fixed to the column tube, and the flat bottom part is fixed to the top part (optionally via the force transmitting means), preferably using the same joining method as used for the fixing to the column tube. In the latter case, only the top part need be capable of absorbing laser light, whereas the material of the bottom part can be selected freely in this regard. The end piece is, besides, preferably designed such that, when it is fixed in the column tube, chromatography fluids can only contact its bottom part. Only the material of the bottom part need then be selected with regard to specific regulations, such as United States Pharmacopeia (USP) Class V or VI, when relevant.

In the following, the invention will be described in more detail, by way of example only, with regard to non-limiting embodiments thereof, reference being made to the accompanying drawings.

BRIEF DESCRIPTION OF THE DRAWINGS

Corresponding parts are designated by the same reference numbers throughout the drawings.

DETAILED DESCRIPTION OF PREFERRED EMBODIMENTS OF THE INVENTION

In the following, terms such as "top", "bottom", upper", lower", etc are used merely with reference to the geometry of the embodiment of the invention shown in the drawings and are not intended to limit the invention in any manner.

Figure 1:
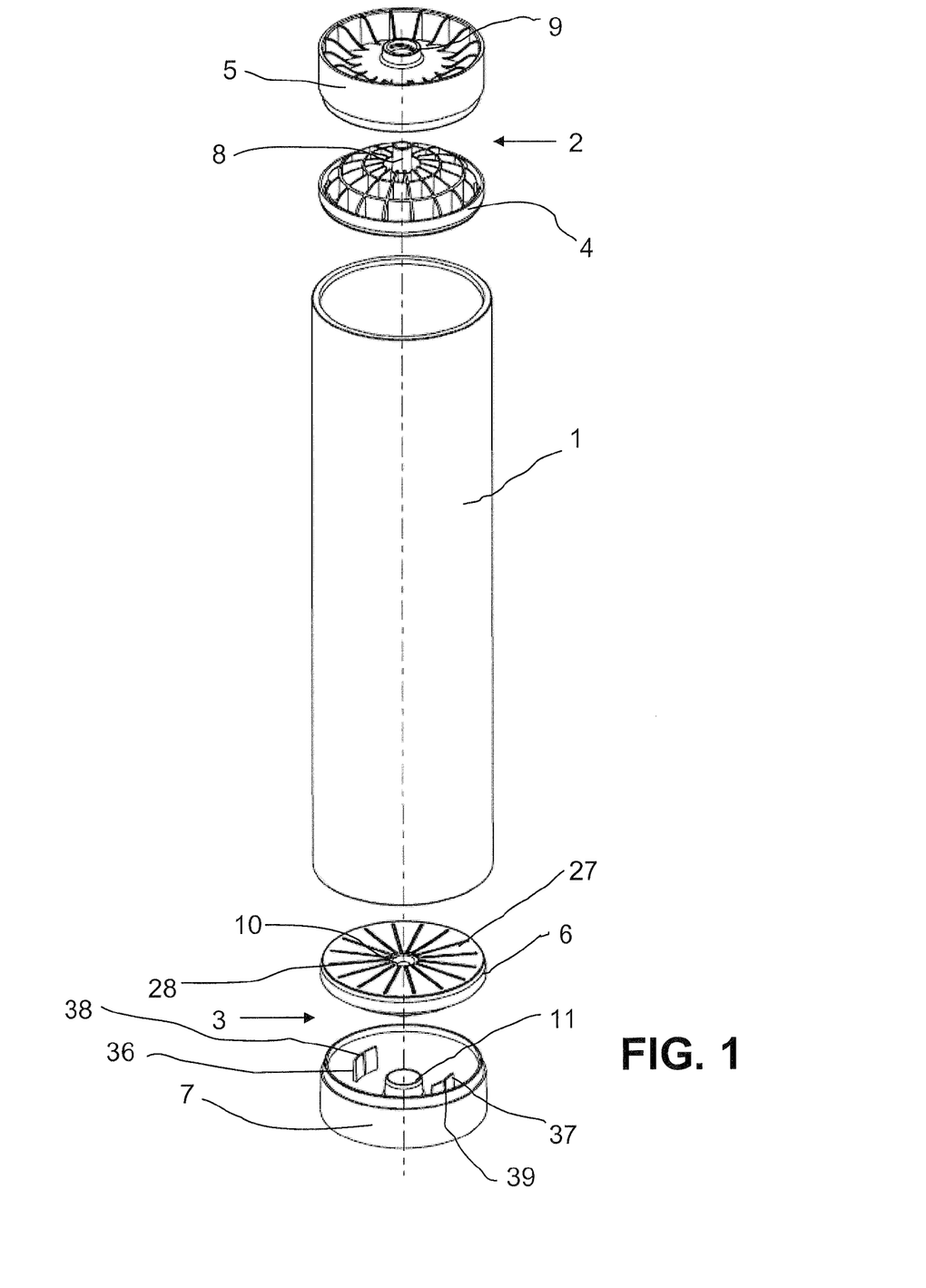
FIG. 1 is an exploded perspective view of an embodiment of a pre-packed chromatographic column according to the present invention.
Figure 2:
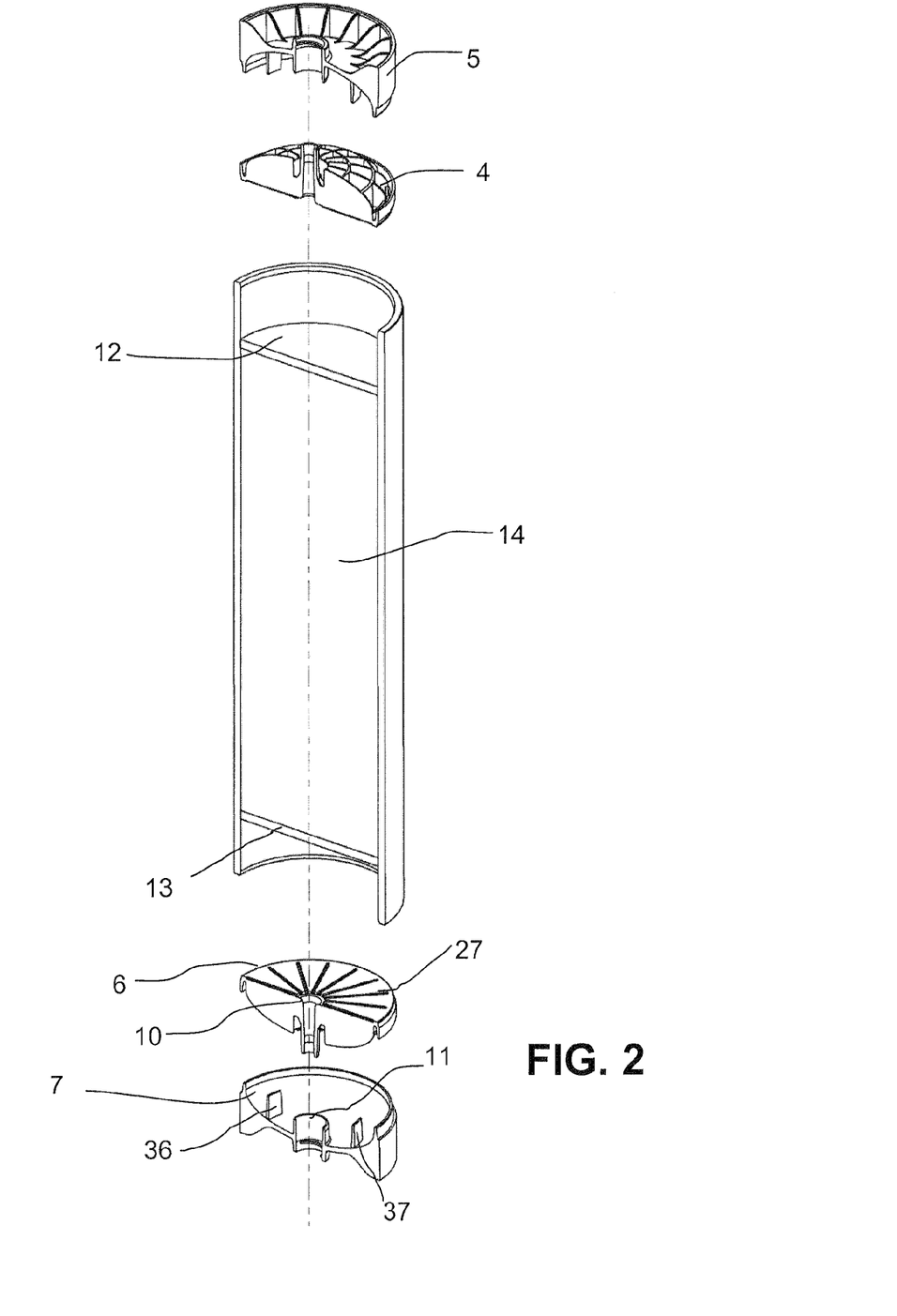
FIG. 2 is a vertical section through the column in FIG. 1.

Referring now to the drawings, and first specifically to FIGS. 1 and 2, an embodiment of a chromatography column, or cartridge, according to the present invention is illustrated in exploded view and comprises a cylindrical plastic tube 1 and, here identical, top and bottom end pieces 2 and 3. The top end piece 2 comprises a cap element 4, in the following referred to as cap, and a dome element 5, in the following referred to as dome. Correspondingly, the bottom end piece 3 comprises a cap 6 and a dome 7. The top cap 4 and dome 5 have respective central coaxial openings 8 and 9 which together form a top inlet of the column. In a corresponding manner, the bottom cap 6 and dome 7 have respective central coaxial openings 10 and 11 which together form a bottom inlet. Located within the tube 1, and supported between top and bottom porous filters 12 and 13, respectively, typically of plastic and hereinafter referred to as frits, is a chromatography media bed 14, e.g. silica. The frits 12, 13 act as sieves which permit chromatography fluids to pass through to the media bed 14 while preventing media in the bed from passing therethrough.

Figure 4:
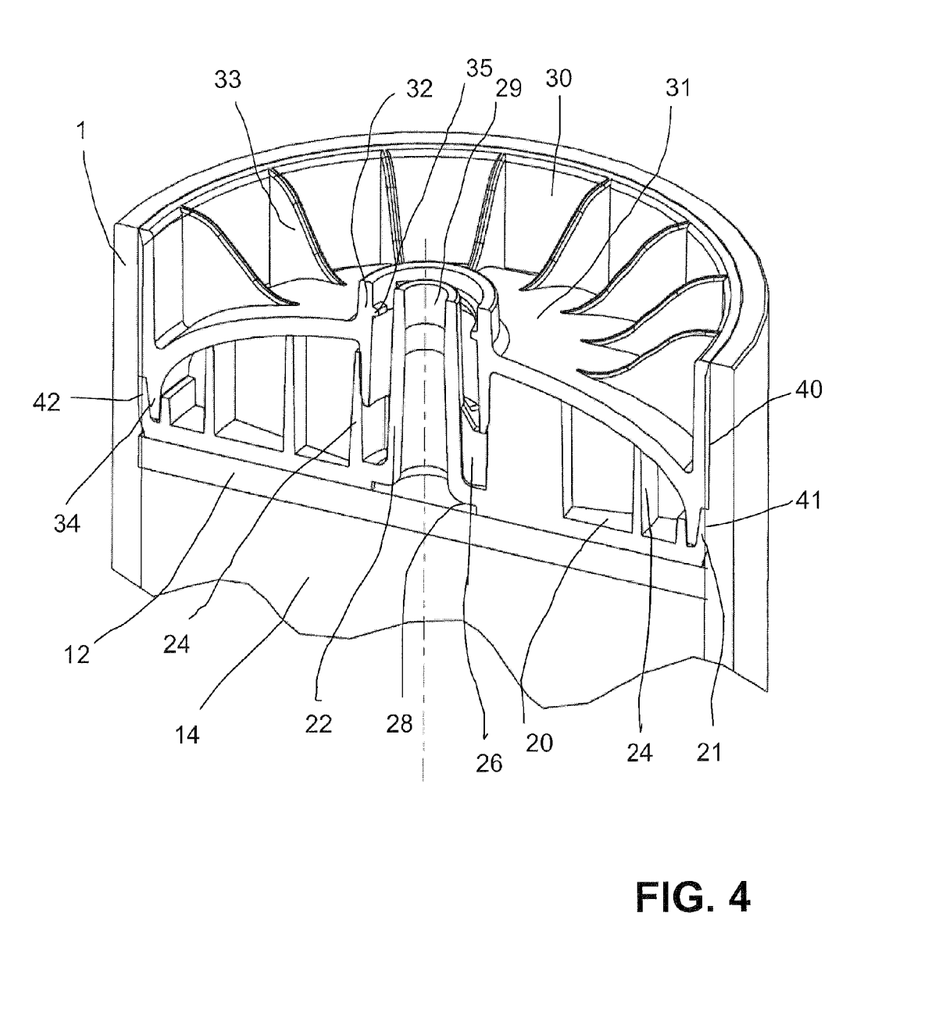
FIG. 4 is a corresponding view to that of FIG. 3 but with the different parts assembled.

The column as assembled is shown in FIG. 4 which illustrates the top part of the column with the top end piece 2 being fitted into the tube 1 and the cap 4 of the end piece contacting the top frit 12. The bottom part is assembled in an analogous manner.

Figure 3:
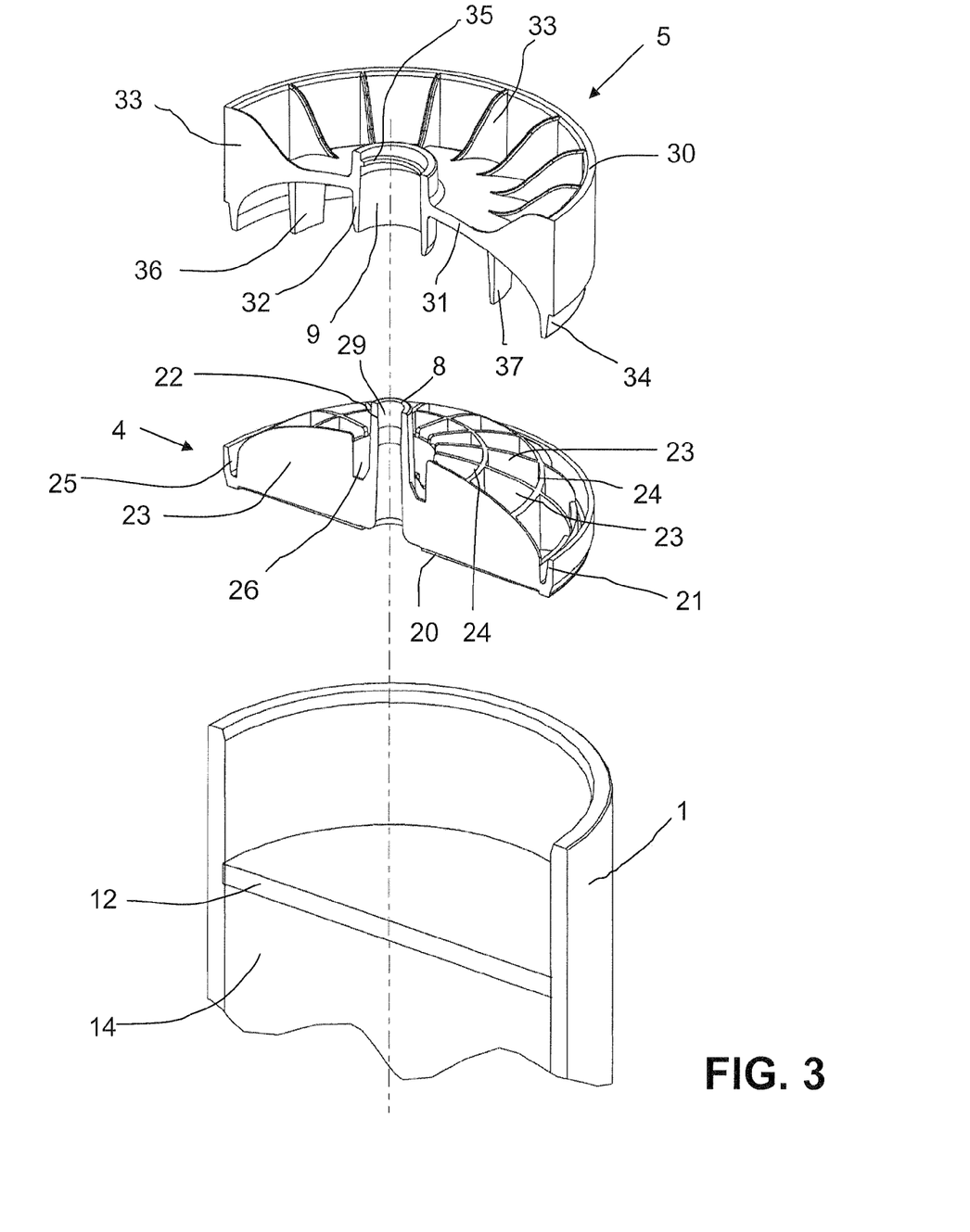
FIG. 3 is an enlarged view of the top part of FIG. 2.

With particular reference to FIGS. 3 and 4, the end pieces 2, 3, here represented by the top end piece 2, will now be described in more detail.

The cap 4 has a circular generally flat base portion 20 with a peripheral upwardly extending rim portion 21, the outer diameter of which corresponds to, but preferably is slightly (e.g. about 1%) larger than the inner diameter of the tube 1 to permit a press-fit as will be described further below. The central opening 8, mentioned above in connection with FIGS. 1 and 2, is defined by an upwardly extending tubular portion 22 which extends to a height substantially above that of the rim 21.

A plurality of stiffening elements, here in the form of a plurality of radial stiffening ribs or flanges 23 and a number of crossing coaxial circular stiffening flanges or rings 24 (here three), project on the upper surface of the base part 20 between the tubular portion 22 and the rim 21. Each radial flange 23 extends in a sloping curved fashion outward from the tubular portion 22 to end just short of the inner edge of the rim 21, defining a slit 25 between the flange end and the rim (FIG. 3). Correspondingly, the heights of the circular flanges 24 decrease stepwise towards the rim 21. The central upper part of the radial flanges 23 extend only to the innermost circular flange 24, while the lower part of the flanges extend up to the tubular portion 22, thereby defining an annular recess 26 therewith.

In the illustrated case, the bottom face of the base part 20 has a plurality of radial fluid distribution grooves or channels 27 (best seen in FIGS. 1 and 2) extending from a central recess 28 around opening 8 (and 10 in FIGS. 1 and 2) towards but not completely up to the peripheral edge of the cap bottom surface. In the assembled state of the column, the non-recessed areas of the cap bottom surface contact, and effectively support, the top surface of frit 12, the flow channels 27 ensuring that fluid entering through the inlet 8 will be evenly distributed across the frit 12. Alternatively, flow distribution channels may be defined against frit 12 by a plurality of radially extending ribs on the cap bottom surface instead of the grooves 27. In still another alternative, there is only recess 28 and no flow channels. Also, differently designed caps may be used in the inlet and outlet ends of the column. For example, a cap with flow channels may be used in the inlet end, and a cap without flow channels in the outlet end.

The upper part of the tubular portion 22 has a tapering inner surface 29 to serve as the female part of a luer type connection for coupling the column into a desired chromatography system.

The dome 5 comprises a cylindrical wall portion 30 which, like the cap 4, preferably has a slightly (e.g. about 1%) larger diameter than the inner diameter of the tube 1 in order to, similarly as the cap 4, fit tightly through a press fit within the tube 1 when the assembled end piece is pressed into position in the tube. A dome-shaped portion 31 extends from the lower part of the wall 30 up to a central tubular portion 32 and is configured to snugly fit on the top surfaces of the radial flanges 23 and the annular flanges 24 of the cap 4. The central tubular portion 32, which extends above and below the dome section 31, defines the previously mentioned opening 9 which is dimensioned to receive the tubular portion 22 of cap 4, while the lower part of the tubular portion 32 will be received in the annular recess 26 of cap 4 when the cap and dome are assembled.

On the top surface of the dome section 31, a plurality of stiffening flanges 33 extend in a radial sloping fashion from the wall 30 towards but not up to the central tubular portion 32. Two opposite guiding elements 36, 37 (see also FIGS. 1 and 2) ensure that, when assembling the cap 4 and the dome 5 (preferably through a press fit), the stiffening flanges 33 on the dome will be in alignment with respective stiffening flanges 23 of the cap, the flanges 33 thereby assisting in resisting the forces transmitted via the flanges 23. In the illustrated case, the guiding elements 36, 37 each consists of a plate-like element with a central vertical slit 38, 39 for receiving a cap stiffening flange 23.

A downward extension 34 of the wall portion 30 has a smaller outer diameter than the wall and is configured to tightly fit against the rim 21 and into the slits 25 between the radial flanges 23 and the rim of cap 4. Similarly, the lower part of the tubular portion 32 fits tightly against an inner surface of the innermost circular flange 24. The upper part of the central cylindrical portion 32 has an inner thread 35 which together with the luer taper 29 of the cap 4 will ensure leakage-proof coupling of the column to a desired instrument system or the like.

The above described structure of the cap/dome assembly is designed to provide for considerable pressure stability. Thus, forces acting upon the flat base member 20 of the cap 4 when the chromatography column is pressurised will be transferred through the stiffening flanges 23 and 24 onto the surface of the dome 5, resulting in substantially only pull stresses in the rounded dome rather than high bending stresses on the cap, as are obtained in a conventional type end piece with only stiffening ribs on an otherwise flat cap.

The design of the cap 4, and particularly the number and shapes of the stiffening flanges, is only exemplary, and may be varied widely, including being replaced by other force transmitting structures. This, of course, also applies to the design and curvature of the dome 5. It is thus well within the skill of a person skilled in the art to optimize the design of the cap/dome assembly for any desired situation. As mentioned above, however, the ratio of dome height to dome diameter should preferably not be less than about 20%.

In the illustrated pre-packed chromatography column, the dome 5 is fixed to the tube 1 in the desired position where the cap 4 presses against the frit 12 on top of the chromatography bed 14. While a number of contactless energy transfer joining methods may be used, this is conveniently performed by laser welding. Laser welding is a technique for welding thin metal or plastic where the required heat is generated by a high-energy laser. This is a well known technique which need not be described in any detail herein.

In brief, laser welding requires one part to be transmissive to a laser beam, and the other part (or a coating at the interface) to be absorptive to the beam. The laser beam passes through the first part and is absorbed by the other part (or the coating) to generate enough heat to soften the interface creating a permanent weld. Typically, semiconductor lasers are used in plastic welding, and the wavelengths used are typically in the range of 800-980 nm. Thermoplastic materials that can be joined include polypropylene (PP), polyethylene (PE), polycarbonate, acrylic (PMMA), polyamide (PA), and acrylonitrile butadiene styrene (ABS), just to mention a few.

In the illustrated case, for joining the dome 5 and the tube 1, the tube 1 is transmissive (a near transparent or translucent plastic) and the dome 5 is capable of absorbing laser light. Unless the material from which the dome 5 is produced is laser absorbing per se, an additive can be added to the material to make it absorptive. Both the cap 4 and the dome 5 are typically formed by injection moulding.

With reference to FIG. 4, the contact area (or part thereof) between the tube 1 and the dome 5, indicated at 40, is irradiated by the laser beam while successively rotating the tube. The laser beam will penetrate the near transparent tube 1 and the laser energy will be absorbed by the dome, resulting in melt between the tube and the dome. For a tight circumferential seam to be obtained, there should be a press fit between the welded surfaces. Optionally, the laser welding operation may be repeated one or more times with successively displaced laser beam to obtain a broader weld seam and/or two or more or separate weld seams.

In a corresponding manner, provided that the cap 4 is made from a laser absorbing material, the cap is joined to the tube 1 by irradiating the contact area (or part thereof) between the rim 21 and the tube 1, indicated at 41 in FIG. 4.

Compared to conventional spin welding, for example, the weld area obtained in laser welding is usually much larger, so that the weld is stronger. While laser welding results in a joint which can be considered to have typically 90-100% strength compared to base material, spin welding will result in about 50-80% strength. As mentioned above, two or more parallel weld seams (or a single broader weld seam) may be obtained by repeating the welding operation with a displaced laser beam.

As an alternative to also fixing the cap 4 to the tube 1, the cap 4 may instead be fixed to the dome 5 at the contact area between dome extension 34 and the rim 21 of the cap, indicated at 42. Although other joining methods like, e.g., gluing, may be contemplated, this is preferably also performed by laser welding, typically after welding the dome 5 to the tube 1. The laser beam then penetrates through the tube 1 and the cap 4 and melts the contact area 42 between the cap and dome, resulting in a pressure tight circumferential seam. Also in this case, a press fit between the welded surfaces is required for a tight seam to be obtained.

Similarly as when welding the dome to the tube, any leakage of fluid into the space between the dome 5 and the cap 4 is prevented so that neither the dome or the weld seam will risk coming into contact with the fluid flow through the column. Therefore, only the cap need be made from a material meeting e.g. USP VI or other requirements, when relevant, while the material for the dome may be selected as desired. For example, the dome material may be a reinforced plastic in order to increase the pressure stability of the dome.

The two-piece design of the dome as described above gives an efficient flat liquid distribution combined with considerable strength (i.e. pressure stability) of the dome.

Optionally, the dome includes a conductive plastic to permit the column to be grounded and decrease problems with static electricity. This may, e.g., be done by adding a conductive substance like e.g. carbon black to the dome material (which also may be used to make a transparent plastic material laser absorbing).

Figure 5:
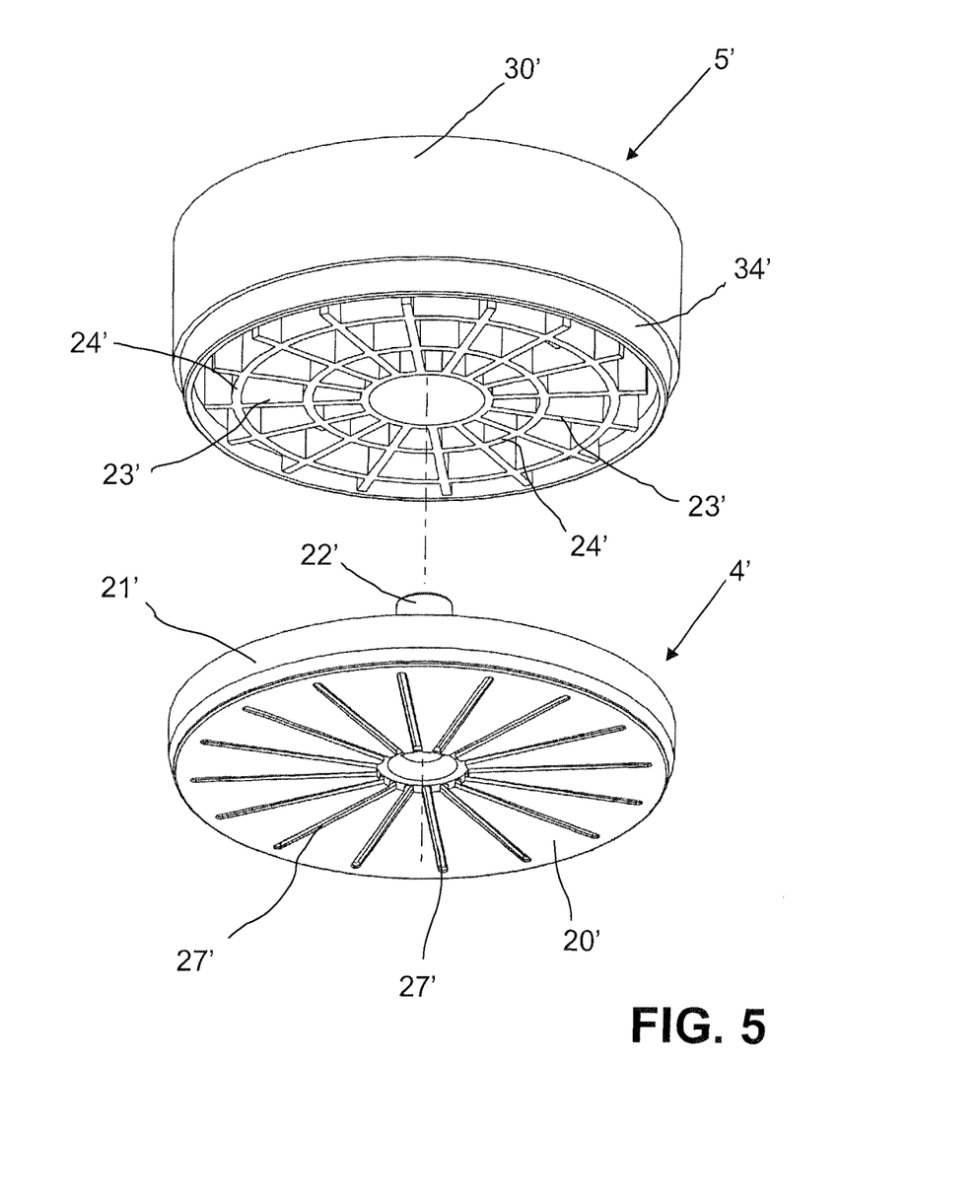
FIG. 5 is an exploded perspective view of an alternative embodiment of an end-piece of a chromatographic column according to the present invention.
Figure 6:
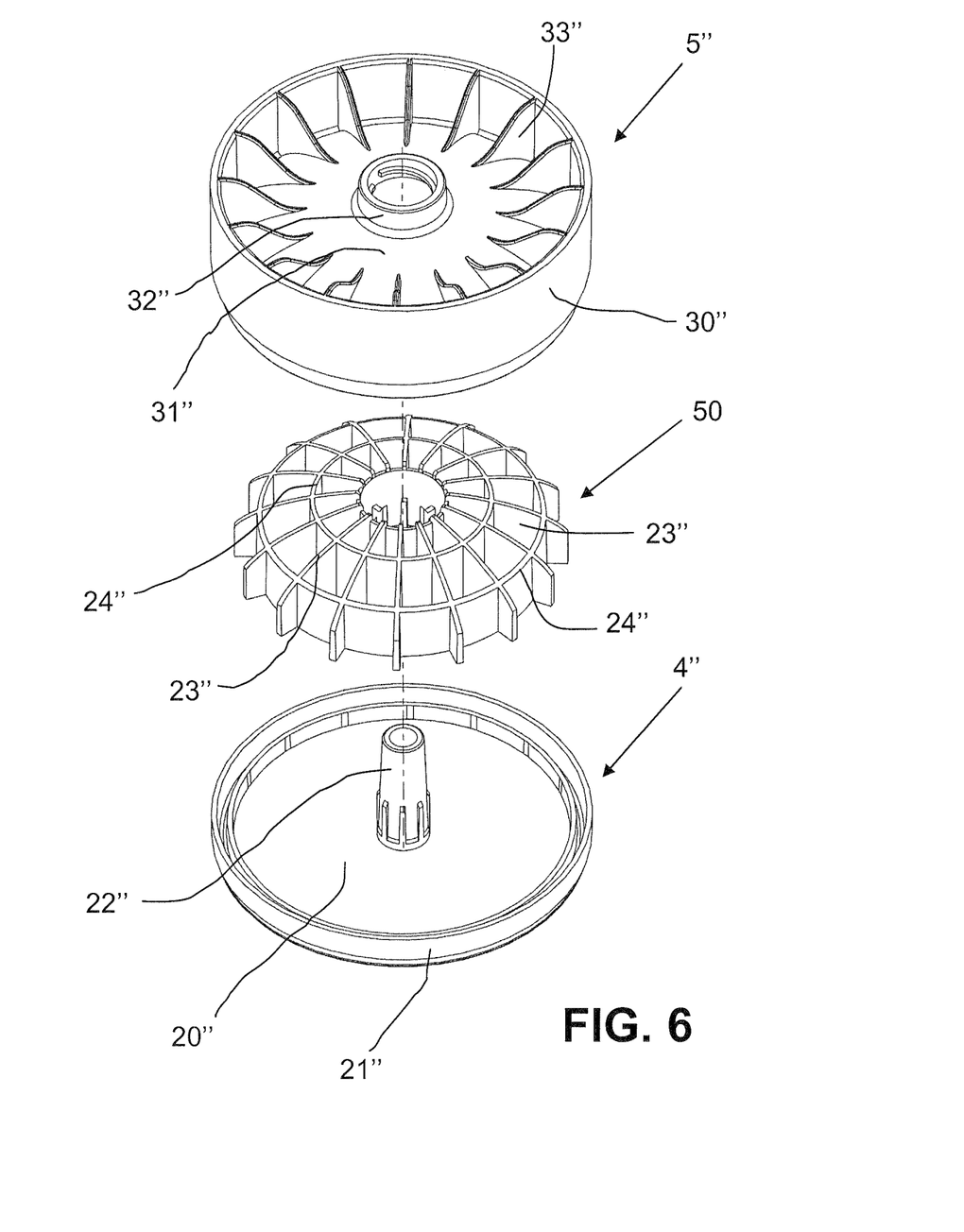
FIG. 6 is an exploded perspective view of still an alternative embodiment of an end-piece of a chromatographic column according to the present invention.

In the cap/dome assembly described above and shown in FIGS. 1 to 4, the force transmitting flange or rib structure 23, 24 is integral with the cap 4. Two alternative embodiments of the provision of the flange or rib structure are illustrated in FIGS. 5 and 6, where corresponding parts have the same reference numerals as in FIGS. 1 to 4, but provided with prime and bis signs, respectively. In FIG. 5, the stiffening flanges or ribs 23', 24' are integral with the dome 5', whereas in FIG. 6, the stiffening flanges or ribs 23", 24" form a separate unit, designated by reference numeral 50.

The above described disposable chromatography column or cartridge is assembled as follows from its components. The tube 1 as well as the caps 4, 6 and domes 5, 7 are all made from a thermoplastic material, e.g. polypropylene or polyethylene. The tube 1 is preferably extruded, whereas the caps and the domes suitably are injection moulded parts. The frits 12, 13 may be porous plastic filters, e.g. of polyethylene. The chromatography medium 14 may be any desired chromatography medium, including rigid media, such as silica, or non-rigid (i.e. compressible) media.

With reference to the Figures, the bottom frit 13 is pressed into place in tube 1. The chromatography medium 14 is then poured into tube 1 from the open top end thereof and packed during vibration, whereupon the top frit 12 is pressed into place against the medium bed 14. The top end piece 2 is then formed by assembling the cap 4 and dome 5 (or cap 4' and dome 5') into each other (or assembling cap 4", dome 5" and the intermediate structure 50). The bottom end piece 3 is assembled in corresponding manner from cap 6 and dome 7. The bottom end piece 3 and the top end piece 2 are then pressed into the filled tube 1 until the two end pieces 2 and 3 are in contact with the respective frits 12, 13. Finally, the cap/dome assemblies 4, 5 and 6, 7, respectively, are successively laser welded to the tube 1 as described above by applying laser light through the tube 1 and rotating the tube 1 at the desired material contact areas to obtain a sealing weld around the tube.

Alternatively, the assembly may start by first inserting the bottom frit 12 and then the bottom end piece 3 and possibly laser welding these components to the tube before continuing with the chromatography medium 14 and the other parts as described above.

For the laser welding, conventional polymer welding equipment may be used, e.g. a commercial system including diode laser LMxxx (140 W, wavelength 938 nm) and laser head LH 50, supplied by Dr. Mergenthaler GmbH, Ulm, Germany.

The chromatography column is then ready for use for flash chromatography and the inlet end can be coupled to desired instrument or other system in per se known manner by a conventional type luer connection, utilizing the tapered section 29 of tubular portion 22, and the threading 35 of the tubular portion 32 of the inlet cap/dome assembly 4, 5. Coupling of the outlet end uses the corresponding parts of the outlet cap/dome assembly 6, 7.

It is readily appreciated that since the cap, dome and frit can be assembled into the column at the same time, the production effectivity is increased.

A great advantage of the chromatography cartridge described above is, of course, that the end pieces (i.e. the cap/dome assemblies) 2, 3 can be pressed into the tube 1 to any packed media bed height, resulting in that any dead volumes will be effectively avoided. Compressible chromatography media may therefore also be used.

The present invention is not limited to the above-described embodiments. Various alternatives, modifications and equivalents may be used. Therefore, the above embodiments should not be taken as limiting the scope of the invention, which is defined by the appending claims.

The invention claimed is:

1. A chromatography column, comprising:
a tubular member having an open inlet end and an outlet end and being adapted to receive a packing material;
a first end piece capable of being inserted through the inlet end of the tubular member;
wherein the end piece includes a first part having a generally flat base portion, a second part having a hollow generally dome-shaped portion having a ratio of dome height to dome bottom diameter of from about 20% to about 50%, and an intermediate structure including radial ribs extending between the first and second parts and configured to transmit pressure forces acting on the flat base portion to the dome-shaped portion to be accommodated thereby,
wherein the first end piece is to be inserted with the generally flat base portion facing inwards towards an interior of the tubular member; and
wherein the first end piece is adapted to be fixed to an inner surface of the tubular member by a joining technique based on non-contact energy transfer.

2. The chromatography column according to claim 1, wherein the outlet end of the tubular member is open, and
the chromatography column further comprises a second end piece corresponding to the first end piece and adapted to be inserted through the outlet end of the tubular member and fixed therein by said joining technique based on non-contact energy transfer.

3. The chromatography column according to claim 1, wherein the force-transmitting intermediate structure is integral with either the first part or the second part, and
wherein the first part and the second part are adapted to be assembled in force transmitting contact with each other.

4. The chromatography column according to claim 3, wherein at least the second part of the end piece is adapted to be fixed to the inner surface of the tubular member.

5. The chromatography column according to claim 1, wherein said joining technique based on non-contact energy transfer comprises laser welding.

6. The chromatography column according to claim 1, wherein the first end piece further comprises a third part having the force-transmitting intermediate structure, and
wherein the first part, the second part and the third part are adapted to be assembled in force-transmitting contact with each other.

7. A pre-packed chromatography column comprising:
a tubular member having an open inlet end and an outlet end;
an end piece inserted through the inlet end of the tubular member,
wherein the end piece includes a first part having a generally flat base portion, a second part having a hollow generally dome-shaped portion having a ratio of dome height to dome bottom diameter of from about 20% to about 50%, and an intermediate structure including radial ribs extending between the first and second parts and configured to transmit pressure forces acting on the flat base portion to the dome-shaped portion to be accommodated thereby,
wherein the end piece is inserted with the generally flat base portion facing inwards towards an interior of the tubular member; and
a chromatography medium packed in the tubular member between the outlet end and the end piece in the inlet end;
wherein the end piece is fixed to an inner surface of the-tubular member by a joining technique based on non-contact energy transfer.

8. The pre-packed chromatography column according to claim 7, further comprising a corresponding end piece fixed to the inner surface of the outlet end of the tubular member by said joining technique based on non-contact energy transfer.

9. The pre-packed chromatography column according to claim 7, wherein said joining technique based on non-contact energy transfer comprises laser welding.

10. The pre-packed chromatography column according to claim 7, wherein the intermediate structure of the end piece comprises an interior rib structure configured to transmit the pressure forces acting on the flat base portion of the end piece to the dome-shaped portion thereof.

* * * * *